(12) United States Patent
Fitzpatrick et al.

(10) Patent No.: US 7,335,516 B2
(45) Date of Patent: Feb. 26, 2008

(54) METHODS TO IMPROVE IMMUNOGENICITY OF ANTIGENS AND SPECIFICITY OF ANTIBODIES

(75) Inventors: Judith Fitzpatrick, Englewood, NJ (US); Regina Lenda, Wesley Hills, NY (US)

(73) Assignee: Serex, Inc., Maywood, NJ (US)

( * ) Notice: Subject to any disclaimer, the term of this patent is extended or adjusted under 35 U.S.C. 154(b) by 883 days.

(21) Appl. No.: 10/224,772

(22) Filed: Aug. 21, 2002

(65) Prior Publication Data

US 2003/0113339 A1    Jun. 19, 2003

Related U.S. Application Data

(62) Division of application No. 09/156,864, filed on Sep. 18, 1998, now Pat. No. 6,455,047.

(60) Provisional application No. 60/090,458, filed on Jun. 24, 1998, provisional application No. 60/059,378, filed on Sep. 19, 1997.

(51) Int. Cl.
*G01N 33/531* (2006.01)
*A61K 38/03* (2006.01)
*C07K 17/02* (2006.01)
*C07K 16/44* (2006.01)

(52) U.S. Cl. ................ 436/547; 435/7.1; 530/345; 530/387.1

(58) Field of Classification Search ............ 424/193.1, 424/130.1, 175.1, 194.1; 530/405, 409, 345, 530/387.1; 436/547; 435/7.1
See application file for complete search history.

(56) References Cited

U.S. PATENT DOCUMENTS

| | | | |
|---|---|---|---|
| 4,647,654 A | | 3/1987 | Knowles |
| 4,727,036 A | * | 2/1988 | Knowles et al. ......... 530/387.9 |
| 5,045,480 A | | 9/1991 | Johnson et al. |
| 5,164,504 A | | 11/1992 | Walling et al. |
| 5,484,735 A | | 1/1996 | Davis et al. |
| 5,646,255 A | | 7/1997 | Klein et al. |
| 5,817,529 A | | 10/1998 | Wu |
| 5,876,727 A | | 3/1999 | Swain et al. |
| 5,929,237 A | | 7/1999 | Kahn |
| 5,955,582 A | * | 9/1999 | Newman et al. ......... 530/387.1 |

FOREIGN PATENT DOCUMENTS

| | | |
|---|---|---|
| EP | 0 185 870 A2 | 7/1986 |
| EP | 0 329 994 A1 | 8/1989 |
| EP | 0 598 329 A2 | 5/1994 |
| WO | WO 92/12975 | 8/1992 |

OTHER PUBLICATIONS

Furth, British Journal of Biomedical Science 1997, 545: 192-200.*
Frantzen, J. Chromatography B, 699 (1997) 269-286.*
Horiuchi, et al., Amino Acids (2003) 25:283-292.*
Wautier et al., Circulation Research, Aug. 6, 2004, vol. 95: 233-238.*
Deyl et al., J. Chromatography B, 699 (1997) pp. 287-309.*
Miksik et al., J. Chromatography B, 699 (1997) pp. 311-345.*
Bjercke, et al., "Stereospecific monoclonal antibodies to nicotine and cotinine and their use in enzyme-linked immunosorbent assays," *J. Immunol. Meth.* 90:203-213 (1986).
Golub, *The Cellular basis of the immune response*, pp. 256-260, Sinnauer Associates, Inc.: Massachusetts, 1977.
Harlow & Lane, *Antibodies A Laboratory Manual*, Cold Spring Harbor: 1988.
Harmon, et al., "The reaction of arylsulfonyl azides with N-methylindole," *J. Org. Chem.* 38: 11-16 (1973).
Javid. et al., "Immunologic characterization and quantification of haemoglobin $A_{1c}$," *Brit. J. Haematology* 38: 329-337 (1978).
Karl, et al., "Development and standardization of a new immunoturbidimetric $HbA_{1c}$," *Klin. Lab* 39: 991-996 (1993).
Kennett, et al., eds., *Monoclonal Antibodies*, Plenum Press: 1980.
Nezlin. *Structure and biosynthesis of antibodies*, pp. 179-186, Consultants Bureau: New York, 1977.
Parker, *Radioimmunoassay of biologically active compounds*, pp. 32-35, Prentice-Hall, Inc.: Englewood Cliffs, NJ, 1976.
Prayfair, "The antibody response," in *Immunology at a Glance*, Blackwell Scientific Publications: London, 1979.
Roitt, *Essential Immunology*, Blackwell Scientific Publications: London, 1971.
Steward & Steensgaard, eds., *Antibody affinity: thermodynamic aspects and biological significance*, CRC Press: Boca Raton, FL. 1983.

* cited by examiner

*Primary Examiner*—Mark L. Shibuya
(74) *Attorney, Agent, or Firm*—Pabst Patent Group LLP

(57) ABSTRACT

A method of improving specific immune responses to small immunogens, haptens, has been developed by changing the linkage between the hapten and carrier being used for immunization. Antibodies to a glycated protein have been developed, utilizing an immunogen which is composed of a glycated peptide mimic of the glycated peptide sequence which is the target epitope, wherein the peptide mimic is constructed to conformationally mimic the conformation of the peptide in the native protein, the peptide mimic contains no charged groups or other immunodominant group, and the peptide mimic is connected to a spacer sequence equivalent to a peptide spacer of between one and thirty amino acids in length, which serves to position the peptide epitope in a conformation that approximates its conformation in the native protein. In a further embodiment the peptide mimic and spacer are linked to a carrier molecule.

4 Claims, 7 Drawing Sheets

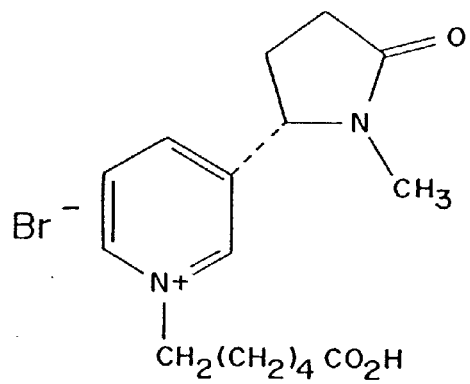
Cotinine Caproic Acid
FIG. 1A
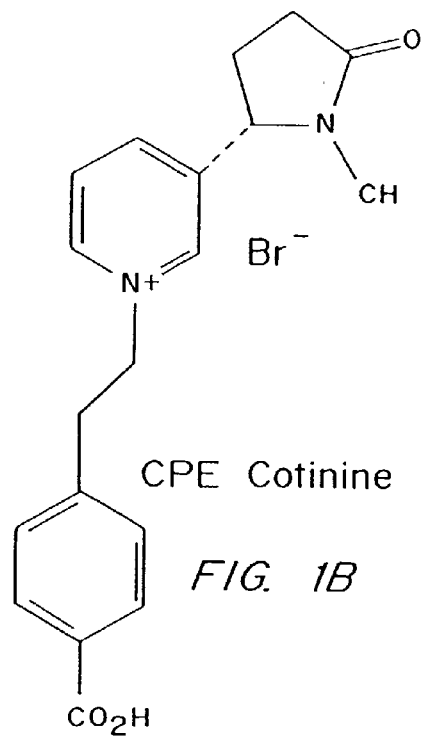
CPE Cotinine
FIG. 1B
FIG. 1C
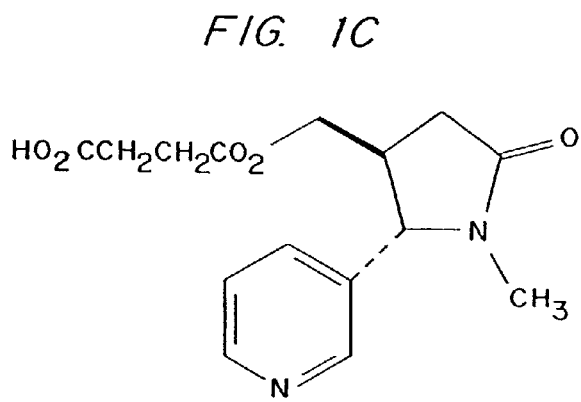
Hydroxymethyl Cotinine Hemisuccinate (HCH)
FIG. 1D
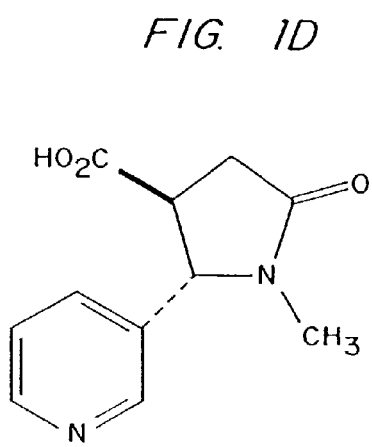
Carboxycotinine

SEQUENCE LISTING

```
<160> NUMBER OF SEQ ID NOS: 8

<210> SEQ ID NO 1
<211> LENGTH: 4
<212> TYPE: PRT
<213> ORGANISM: Homo sapiens

<400> SEQUENCE: 1

Val His Leu Thr
1
```

<210> SEQ ID NO 2
<211> LENGTH: 15
<212> TYPE: PRT
<213> ORGANISM: Homo sapiens

<400> SEQUENCE: 2

Val His Leu Thr Pro Glu Glu Lys Ser Ala Val Thr Ala Leu Trp
 1               5                  10                  15

<210> SEQ ID NO 3
<211> LENGTH: 11
<212> TYPE: PRT
<213> ORGANISM: Homo sapiens

<400> SEQUENCE: 3

Val His Leu Thr Pro Glu Glu Lys Tyr Tyr Cys
 1               5                  10

<210> SEQ ID NO 4
<211> LENGTH: 10
<212> TYPE: PRT
<213> ORGANISM: Homo sapiens
<220> FEATURE:
NAME/KEY: MISC_FEATURE
LOCATION: (2)..(2)
<223> OTHER INFORMATION: 2-amino-3-furanylpropionic acid

<400> SEQUENCE: 4

Val Xaa Leu Pro Pro Glu Glu Tyr Tyr Cys
      1               5                  10

SEQ ID NO 5
LENGTH: 10
<212> TYPE: PRT
<213> ORGANISM: Homo sapiens

<400> SEQUENCE: 5

Val His Leu Thr Pro Glu Glu Tyr Tyr Cys
      1               5                  10

SEQ ID NO 6
<211> LENGTH: 10
<212> TYPE: PRT
<213> ORGANISM: Homo sapiens

<400> SEQUENCE: 6

Val Phe Leu Thr Pro Glu Glu Tyr Tyr Cys
      1               5                  10

<210> SEQ ID NO 7
<211> LENGTH: 10
<212> TYPE: PRT
<213> ORGANISM: Homo sapiens

<400> SEQUENCE: 7

Val His Leu Pro Pro Glu Glu Tyr Tyr Cys
 1               5                  10

<210> SEQ ID NO 8
<211> LENGTH: 10
<212> TYPE: PRT
<213> ORGANISM: Homo sapiens

```
<400> SEQUENCE: 8

Val Phe Leu Pro Pro Glu Glu Tyr Tyr Cys
 1               5                   10
```

METHODS TO IMPROVE IMMUNOGENICITY OF ANTIGENS AND SPECIFICITY OF ANTIBODIES

CROSS-REFERENCE TO RELATED APPLICATIONS

This application is a divisional of prior application U.S. Ser. No. 09/156,864 filed Sep. 18, 1998, now U.S. Pat. No. 6,455,047. by Judith Fitzpatrick and Regina B. Lenda, which claims priority to U.S. Ser. No. 60/059,378 entitled "Method to Improve Immunogenicity of Antigens and Antibody Responses" filed Sep. 19, 1997 by Judith Fitzpatrick and to U.S. Ser. No. 60/090,458 entitled "Immunoassay and Antibody Specific for Hemoglobin A1c" filed Jun. 24, 1998 by Judith Fitzpatrick and Regina B. Lenda.

BACKGROUND OF THE INVENTION

Methods for making antibodies are well known and have become routine for most antigens. However, some antigens, due to small size, conformation changes under different conditions, or low immunogenicity—for example, highly conserved protein or proteins which are heavily glycosylated, have not been easy to make highly specific antibodies to.

A number of methods have been developed to address this problem. For example, it is well known that haptens or small molecules such as peptides and drugs are not immunogenic unless conjugated to a protein. Such proteins are designated as carrier proteins and such conjugated haptens as immunogens. However, it has been discovered that conjugation can alter not only the charge but also the conformation of the hapten, thereby generating antibodies that recognize the free hapten to a lesser extent than the immunogen.

The high immunogenicity of most linkers has also been a major obstacle to generating monoclonal antibodies for haptens of small size, e.g. cotinine, for which both the yield of useful clones and the affinities of available monoclonal antibodies are low. Thus, it has proved very difficult to raise monoclonal antibodies to many drugs and to manufacture peptide vaccines that will induce neutralizing antibodies to infectious agents.

Many commercial assays require highly specific antibodies, particularly for use in chromatographic assays where the result is to be indicative of a quantitative value, not just qualitative. For example, diabetes is a severe, life-threatening, chronic disease resulting from an impairment of the body's ability to turn glucose into usable energy. Type II diabetes is the most common form of diabetes. Up to 95 percent of the 16 million Americans with diabetes have Type II. It is also known as adult-onset diabetes, as it usually develops in people over the age of 45. In addition to age, weight and lack of physical activity or exercise, heredity also plays a role in a person's risk of having the disease.

Heart disease, stroke, kidney disease, blindness, circulatory and nerve problems are linked to long-term, high levels of blood sugar (hyperglycemia). Co-morbid conditions often include hypertension, high cholesterol and triglycerides. Hemoglobin A1c (HbA1c) testing has great importance in the overall management of diabetes since HbA1c reflects the portion of glucose that attaches itself to hemoglobin. It has been shown to accurately and reliably reflect long term levels (2-3 months) of chronic hyperglycemia. Therefore, while daily glucose monitoring is required for immediate intervention, HbA1c levels are considered a more accurate indicator of an individual's long term blood glucose levels.

In addition to other in-office and at-home tests, the American Diabetes Association (ADA) recommends HbA1c testing four times a year for insulin-treated patients and at least twice yearly for all other patients with diabetes, or as often as needed to help achieve good glycemic control.

Just recently HbA1c has been approved for screening for diabetes. It is estimated that at some time during their lives approximately 10% of adults will develop adult onset diabetes. Most of these individuals are diagnosed after 10-15 years of hyperglycemia when the condition results in sugar in the urine. Damage is being done during the undiagnosed period. HbA1c screening could identify such individuals much earlier. Research shows that the HbA1c test can provide information that in many cases can help health care providers and patients develop regimens that dramatically lower the risks for serious and life-threatening diabetes complications, including blindness, kidney disease and nerve damage. Each year, diabetes results in 54,000 leg and foot amputations. Diabetes is the leading cause of end-state renal disease (kidney failure). It is the fourth leading cause of death by disease in the United States.

A landmark study known as the diabetes Control and Complication Trial (DCCT) revealed a direct correlation between high blood sugar levels and the development of long-term complications in people with Type I or insulin-dependent diabetes mellitus; there is no reason to believe that the effects of better control of blood glucose levels would not also apply to patients with Type II diabetes. The DCCT also found that, through blood glucose and regular HbA1c testing, adjustments could be made in diet, exercise or insulin dosage to reduce diabetes-associated risks. These include reductions in eye disease by up 76 percent, kidney disease by 56 percent and nerve damage by 60 percent.

Due to the complexity of existing HbA1c tests, they are generally performed in clinical laboratories and at significant costs. Since physicians treating individuals with diabetes rely on this test for the management of the patient's disease, it is desirable for it to be performed quarterly. Additionally, patients' interest in knowing their HbA1c number has increased largely as a result of the DCCT study. Most Type I (insulin dependent diabetic) know their HbA1c number just like they know their blood pressure or cholesterol level.

Hemoglobin A1c (Hb $A_{1c}$) is one form of hemoglobin. It is identical to Hemoglobin $A_o$ (Hb $A_o$) with the exception that the N-terminal valine on the â chain is linked to C-1 of fructose through the amino group. This glycation causes a change in charge, which resulted in its first identification as the A1c fraction on an ion exchange column procedure. The formation of valine-fructose residue is believed to result from the formation of a Schiff base between valine and glucose followed by an Amadori rearrangement. The process is irreversible and the ratio of Ha $A_{1c}$ constitutes 4-6% of the total Hb. In diabetes patients, the ratio increases two to three fold to 6-15%.

The first step to develop an immunoassay in a Point of Care (POC) format to determine this ratio, i.e. Hb $A_{1c}$/total Hb, is to develop an antibody that can discriminate between the native conformations of HbAo and Hb $A_{1c}$. Critical to providing a test for screening are low cost reagents. The current assays for HbA1c entail expensive and/or cumbersome physical methods such as ion exchange and column chromatography, or almost equally cumbersome and therefore non cost effective immunoassays. Thus while antibody based assays have traditionally offered an economical alternative to physical methods, as will be discussed below, currently available antibodies do not offer the traditional advantages of specificity, economy and ease of use. Thus there is a need for an antibody that would offer ease of use, economy and specificity. Such an antibody would enable both Point of Care testing and adaptation of a HbA1c assay to any of many automated immunoassay systems.

There are several problems to be addressed when making an antibody to HbA1c or other antigens like HbA1c. The hemoglobin molecule is a poor immunogen because the hemoglobin sequence is highly conserved and it is difficult to overcome tolerance of self. The peptide sequence of the HbA1c epitope, hereafter the HbA1c epitope, is the same in mouse and human and most mammals: sheep have a different sequence in this epitope region of the N terminal. It is difficult to overcome tolerance of self. Even though most animals do not form HbA1c, it is not possible under normal conditions to use Hb $A_{1c}$ directly as the immunogen to make an antibody that can discriminate HbAo from HbA1c since the difference between A1c and Ao is only the addition of one glucose molecule. Fructose has low immunogenicity and so the dominant immune response is postulated to be to more immunodominant areas of the epitope.

A glycated site is not a good epitope: the HbA1c epitope comprises less than 1% of the hemoglobin surface. Therefore one must immunize with a peptide. It is difficult to make an antibody to a peptide that has high affinity for the peptide sequence of the native protein. The antibodies currently commercialized fall into two categories, polyclonal and monoclonal.

Boehringer Mannheim (BM) markets a turbidometric assay kit which utilizes a sheep polyclonal antibody. A sheep polyclonal prepared to $HbA_{1c}$ whole molecule is described by Javid et. Al. (*Brit. J. Haematology:* 38:329-337 1978) and U.S. Pat. No. 5,646,255 to Klein, et al. The BM antisera was raised to the reported immunogen sequence "Fructose Val His Leu Thr . . . " (SEQ ID NO:1) (Karl, et al. Klin. Lab 39:991-61993). It is probable that this antibody can be successfully raised in sheep because sheep do not have the same amino terminal sequence as other mammals and hence they are able to recognize as foreign and immunologically response to the common mammalian N terminal sequence, "Val His Leu Thr" (SEQ ID NO:1). The mouse in which monoclonals are raised has the same sequence as humans and most other mammals and this probably explains why, when the same immunogen is used to immunize mice, that the majority, if not the only, antibodies that are produced, react with the denatured form of hemoglobin (which is foreign) but not the native conformation (which is not foreign). It should also be pointed out that all monoclonal antibodies are screened for in an Elisa format because that is the only truly economical method for performing all the screening that must be done during the course of making a monoclonal. The Elisa plate is coated with the hemoglobin or protein: hemoglobin is not in its native conformation, i.e., it denatures, when coated on an Elisa plate. Thus even if the mouse did produce a few clones that had the potential to recognize the native conformation, the screening process works to select for clones that recognize the denatured configuration and thus against selection of a clone that would recognize non denatured or native HbA1c.

The BM antibody does not show high specificity: In the experimental Elisa system described herein, this sheep polyclonal antibody shows that about 10-20% cross reacts with $HbA_o$ and reacts equally well with native (i.e. $HbA_{1c}$ that is not specifically subjected to denaturing conditions) and denatured $HbA_{1c}$. The BM antibody is commercialized in a turbidometric assay. These are liquid based assays that are run on an autoanalyzer and require less than 10 minutes. In such a system one can often disregard low level cross reactivity because cross-reactive moieties having lower association constants exert less interference in shorter assays. However, it would be difficult to utilize such an antibody in anything but an autoanalyzer assay, because to compensate for such high cross reactivity, all assay conditions, the time, pH, temperature, sample dilution, etc., must be carefully controlled, as they are on an autoanalyzer. In a point of care assay, it is not possible to dilute the sample or to add large amounts of buffering materials or to carefully control time and temperature. Thus cross reactivity becomes a much larger problem under assay conditions that are not ideal.

A further disadvantage of the BM polyclonal antibody is that it is not cost effective. The kit provides the exceptionally large amount, 40 µg, of purified antibody for each assay. Polyclonal antibody that must be purified and provided at such high concentration is very expensive. Point of Care assays, which usually require much larger amounts of antibody than laboratory assays, generally have less than 1 µg/assay. The large amount of antibody required by the BM test is probably due to low affinity of the antibody. Low affinity antibody generally means that the assay lacks a high degree of specificity. Indeed, it is well documented that all the currently commercialized immunoassays for HbA1c are lacking in specificity; i.e. they do not discriminate as well as required between various modifications of the N terminal valine.

Thus, while polyclonal antibody raised in sheep has the advantage that it can recognize native HbA1c sequence, it has the disadvantages that it is very expensive and that it lacks specificity and thus is limited to formats that can compensate for these restrictions on its performance. More importantly, polyclonal antibodies to one discrete conformational epitope cannot provide the consistency that is required by today's clinical laboratory standards, i.e. by definition, polyclonal antibodies contain many clones of different affinity and each animal at each bleed provides a mix of clones that unique to that bleed. When there is only one epitope and that epitope is conformational, polyclonal antibodies generally provide unacceptable variations in reagents from lot to lot.

A monoclonal antibody to HbA1c would have the potential to overcome the cost and consistency problem of polyclonal antiserum but thus far all available and described monoclonals recognize altered HbA1c and require either a 10 minute denaturation process or protease treatment to render the sample suitable for testing with the antibody. The requirement for pretreatment of sample precludes the adaptation of these antibodies to Point of Care Tests; non-laboratory personnel in a non-laboratory environment cannot be expected to treat the sample. Pretreatment also greatly limits the usefulness of such antibodies in screening assays and pretreatment adds significant cost and complexity to the test.

Monoclonal antibodies specific for the glucosylated N-terminal peptide residue in $HbA_{1c}$ are described in U.S. Pat. No. 4,727,036 to Knowles. These antibodies are hereafter referred to as the Miles Antibody. The Miles antibody was produced using the glycated N-terminal fragment of alpha chain as the immunogen. The first 15 amino acids of alpha chain N-terminal are Val-His-Leu-Thr-Pro-Glu-Glu-Lys-Ser-Ala-Val-Thr-Ala-Leu-Trp. (SEQ ID NO:2) The Miles Antibody was produced to a peptide sequence that included the first 8 amino acids: BM also utilized only the first 7 or 8 amino acids. Miles' $HbA_{1c}$ specific antibody is a monoclonal antibody which reacts only with denatured HbA$_{1c}$ (the kit requires 4 minutes with a chaotropic agent and it interacts with HbA1c immobilized on microtiter plate. The Miles antibody discriminates with great specificity between HbA$_o$ and HbA1c when these proteins are denatured. This antibody shows almost no cross reactivity with HbA$_a$ in our experimental Elisa assay. However it does not function as a diagnostic reagent unless the reagents are denatured. The patented immunogen for the Miles monoclonal is fructose-Val-His-Leu-Thr-Pro-Glu-Glu-Lys-Tyr-Tyr-Cys. (SEQ ID NO:3) (Tyr-Tyr is commonly used to obtain spacing of immunogen from the protein carrier). This is essentially the same immunogen described in the literature for producing polyclonal antibody to HbA1c and used by BM to produce sheep polyclonal. This monoclonal antibody recognizes the amino terminus in denatured HbA1c. Thus the sample requires pretreatment to allow interaction with the antibody. This pretreatment step renders the test of limited economic value. Further the literature indicates that the antibody recognizes other modifications of the terminal valine containing peptide: this indicates that the antibody recognizes modification of the N terminal, not the specific modification.

Generally speaking, antibodies made to linear peptide analogs of epitopes are of low affinity and thus lack specificity i.e. they will show high cross reactivity. In this case that means that the antibody made to HbA1c would be expected to recognize both HbAo and HbA1c. The monoclonal antibody described in patent U.S. Pat. No. 4,647,654 to Knowles, marketed by Miles, does not distinguish between Ao and A1c unless they are denatured; in the denatured form the peptide appears to the antibody as similar to the immunogen.

It is therefore a first object of the present invention to provide a method for making antibodies to immunogens that have low immunogenicity.

It is another object of the present invention to provide methods and reagents to enable generation of high titer antibodies to preferred epitope conformations, especially those where the conformation is altered by conjugation to carrier or by denaturation.

It is a second object of the present invention to produce a monoclonal antibody that reacts with antigens such as native HbA1c, that is both more accurate and sensitive than the antibodies used in currently available tests, and yet at the same time is cheaper to produce and use.

It is a further object of the present invention to provide an antibody that is useful in a point of care test and thus does not require any treatment and must react with the native molecule.

It is still another object of the present invention to provide a method and reagents to quickly and inexpensively measure antigens such as Hb A1c and to determine the ratio of antigens such as Hb A1c and Hb Ao.

SUMMARY OF THE INVENTION

Methods are described herein to enhance the specificity of monoclonal antibodies to antigens characterized by low immunogenicity or which do not elicit production of highly specific antibodies with little cross-reactivity. Examples of such antigens include glycosylated proteins, proteins which are highly conserved among species, and very low molecular weight proteins which are immunogenic only as haptens conjugated to carrier molecules.

In a first method, the initial immunization is performed with a first immunogen and the second, "boosting" immunization is performed with a slightly different immunogen which shares in common with the first immunogen the epitope(s) to which an antibody response is desired. In a second method, the immunogen is modified so that immunodominant epitopes are altered, resulting in an antibody response to an epitope which is present in both the denatured or native proteins or which is obscured in the more immunogenic derivative used for the initial immunization.

In the examples using cotinine and hemoglobin, immunization protocols are described in which the initial immunization is performed with one immunogen and boosting is done with a second immunogen of a different structure. In the first embodiment, the structural alteration is confined to the linker while the hapten and the carrier protein remain unchanged. The method thus overcomes problems resulting from conformational changes, linear-specific antibodies and low immunogenicity of haptens. This protocol was found to produce superior antibody responses to, and be particularly useful and effective, with small haptens such as cotinine.

A method of producing an antibody to a glycated protein has also been developed, which utilizes an immunogen which is composed of a glycated peptide mimic of the glycated peptide sequence which is the target epitope within a larger protein, wherein the peptide mimic is constructed to conformationally mimic the conformation of the peptide in the native protein, the peptide mimic contains no charged groups or other immunodominant group, and the peptide mimic is connected to a spacer sequence equivalent to a peptide spacer of between one and thirty amino acids in length, which serves to position the peptide epitope in a conformation that approximates its conformation in the native protein. In a further embodiment the peptide mimic and spacer are linked to a carrier molecule. This method has been used to produce an antibody to the glycated protein HbA1c, wherein the peptide mimic includes a valine modified by addition of a glucose molecule, an analog of Histidine which does not bear a charge in the immunizing structure, allowing orientation of the peptide so that the immune response can be directed to the side of the peptide chain oriented oppositely to the ring, and is of a size that the conformation of the peptide mimics the conformation of the peptide in the native molecule, a leucine or an analog thereof which allows binding to an antibody preferentially recognizing Hb A1c such as 82D259, and a threonine or an analog thereof which allows binding to antibody number 82D259. In the example described below the histidine analog is 2-amino-3-furylpropionyl, and the peptide is Fructosyl-Val-2-amino-3-fur-anylpropionic acid-Leu-Pro-Pro-Glu-Glu-Tyr-Tyr-Cys (SEQ ID NO:4).

In a preferred method of immunizing to a glycated peptide linked to a carrier protein, the portion of the peptide that serves to link the peptide to the carrier protein is selected to provide minimal antigenic competition for immune response and to maintain the epitope portion of the molecule in the configuration that it appears on the surface of the molecule. Further in the method of immunizing to a glycated peptide linked to a carrier protein, the method of linkage of the peptide to the carrier protein is changed from the first to the second immunizing doses to avoid boosting to the linker specific antibodies and to avoid boosting to a linker induced epitope conformation.

BRIEF DESCRIPTION OF THE DRAWINGS

FIGS. 1A-1D are structures of cotinine derivatives: cotinine caproic acid (FIG. 1A), CPE cotinine (FIG. 1B), hydroxymethyl continine hemisuccinate (HCH) (FIG. 1C), and carboxycotinine (FIG. 1D).

DETAILED DESCRIPTION OF THE INVENTION

Antigens

Figure 2:
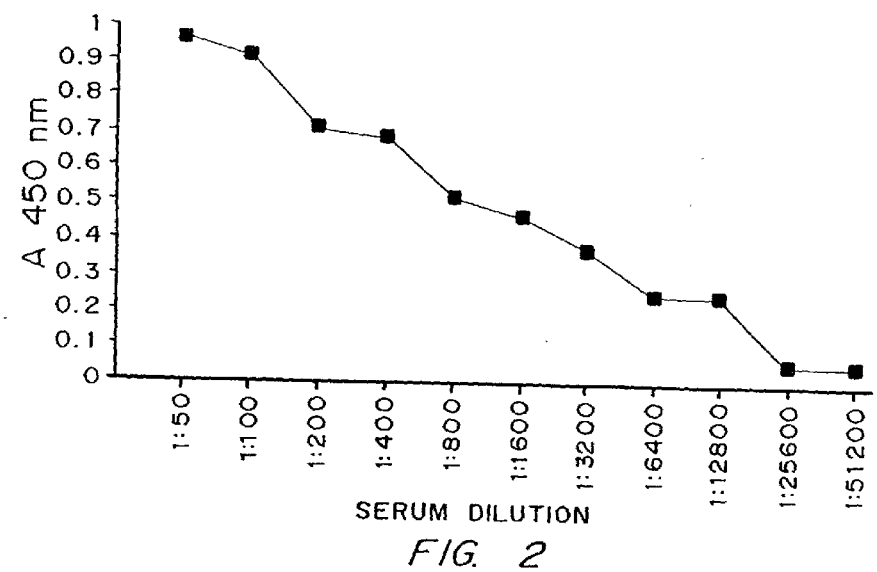
FIG. 2 is a graph of the antibody titer produced in mice immunized with carboxy-cotinine-KLH.

The following definitions are provided:

A hapten is a molecular moiety of less than 10,000 molecular weight, most often of less than 2,000 molecular weight.

A hapten analog is used herein to refer to a hapten which has been modified but retains essentially the same immunological characteristics of the hapten of interest.

An epitope is a chemical conformation, for example 4 to 12 amino acids, recognized by an antibody.

A carrier molecule is a large molecule, generally greater than 40,000 molecular, for example, a large peptide, protein or particle, which is sufficiently large that multiple haptens can be conjugated to it. Examples include polylysine, keyhole limpet hemocyanine, and bovine serum albumin.

An antigen elicits an immune response in the form of an antibody.

A linker is a molecule connecting two other molecules, for example, the antigen and a carrier molecule.

A linkage is the direct chemical coupling between two molecules, for example, a hapten and a carrier molecule, in which the conformation of the hapten may be influenced by the nature of the chemical linkage.

Antigens can be proteins, synthetic organic molecules, metals, and sugars, alone or in combination with proteins. Preferred antigens for use in the methods described herein glycated hemoglobin and other glycated proteins, amphetamines and other drugs which do not elicit highly specific antibodies or which might be poorly immunogenic. Another preferred antigen is where the desired response is to one or more epitopes in a protein, for example, in a vaccine, not to all of the epitopes present in the protein.

Methods of Modifying Antigens to Enhance Immunogenicity

Conjugation

Numerous conjugation methods are known in the art and are described, for example, by G. T. Hermanson in "Bioconjugate Techniques", Academic Press, 1996. Briefly, conjugations of a hapten to a carrier is generally effected by means of linkers or, more appropriately cross-linkers, which consist of linear molecules of various length bearing reactive functional groups at both ends. In homobifunctional linkers (i.e. glutaraldehyde) the two functional groups are identical: in heterobifunctional linkers, they are different. The detailed conjugation chemistries are well known. The final conjugation product can be thus depicted as hapten—linker$_y$—carrier$_z$ (H-L-C), for example, where H is a cotinine derivative, L is a crosslinker and C is keyhole limpet hemacyanin (KLH). The dashes represent covalent bonds; x and y are identical and generally much larger than z.

Derivatization

Immunogens can be modified as described below by substitution or deletion of specific amino acid residues, chemical coupling of blocking agents, sugars, linkers and/or carrier proteins, and other methods known to those skilled in the art. These are screened for binding to antibodies which are known to have a desired specificity and the results compared with binding to the molecule which is to be quantitated, for example, using standard immunoassays or other means of quantitation as demonstrated in the example.

Methods for Producing Antibodies

The science, or more properly, the art of antibody production has progressed over the past decades. Well established and tested procedures are provided, e.g. in "Antibodies-A Laboratory Manual", E. Harlow and D. Lane, Cold Spring Harbor, 1988 and in "Monoclonal Antibodies", R. H. Kennett et al., eds., Plenum Press, 1980. The more theoretical aspects of antibody production are discussed in "Antibody Affinity": Thermodynamic Aspects and Biological Significance", M. W. Steward and J. Steensgaard, CRC Press, 1983, the teachings of which are incorporated herein by reference.

The present invention will be further understood by reference to the following non-limiting examples making antibodies to cotinine and hemoglobin.

EXAMPLE 1

Preparation of Cotinine Derivatives which Yield more Specific Antibodies to Native Cotinine Over the past 15 years, SEREX™ has successfully produced several polyclonal antibodies for cotinine, but has consistently failed in numerous attempts to raise monoclonal antibodies using conventional protocols. Other investigators, e.g. J. J. Langone, J. Immunol. Meth. 90, 203-213 (1986), also obtained cotinine monoclonal antibodies, but these antibodies are linker specific. U.S. Pat. No. 5,164,504, assigned to Abbott, disclosed preparation and use of two cotinine immunogens which yielded antibodies with very low titers. Monoclonal cotinine antibodies are commercially available, but have little or no practical utility.

Possible explanations for the problems with cotinine are its small size and low immunogenicity. Cotinine, a major metabolite of nicotine, is also structurally related to several nicotinic acid derivatives which are present in mammalian plasma and tissues. Using conventional immunization protocols, SEREX™ has never succeeded in producing monoclonal or polyclonal antibodies in mice or rabbits with titers of >1:5000 even after several boosts over a period of six months. Furthermore, the resultant antibodies consistently reacted with the linker and generally were of low affinity. The monoclonal antibody described by Langone (cited above) reacted strongly with the linker portion as evidenced by high crossreactivity with the drug metyrapone.

In contrast, the approach described above yielded concentrations of monoclonal antibodies equivalent to titers of 1:100,000 after a single boost with the second immunogen which differed from the first immunogen only in the structure of the linker ($L_2$ versus $L_1$ in H-L-C). This procedure yielded many clones of high titer and specificity. The dramatic improvements in immune responses obtained with the protocol were totally unexpected and are contrary to conventional wisdom which prescribes boosting with the same type and preferably the identical preparation or lot of immunogen. It is believed that this method overcomes the problem of linker specific antibody as well as linker specific conformation of hapten and propose that it will prove a useful strategy for immunization with any small molecule drug or peptide which is conjugated to a carrier for immunization.

It is believed that boosting with the altered immunogen of this immunization protocol stimulates clones specific for H and C, which are common to both immunogens, but not clones specific for $L_1$ which remain at the low pre-boost levels. Boosting with the $L_2$ linker in the second immunogen mounts a weakened response to $L_2$, in relation to the $L_1$ response, whereas there is the expected dramatic increase in the responses to H (and C), thus yielding antibody clones with high titers and recognition for cotinine, but very low recognition of both linkers.

Preparation of Cotinine Derivatives

Preparation of Cotinine Caproic Acid

As shown in FIG. 1A, the mixture of cotinine (106 mg) and bromohexanoic acid (117 mg) in 1 mL of DMF was heated at 100° C. overnight. The mixture was allowed to cool to room temperature and the solvent was removed under reduced pressure. The residue was rinsed with $CH_2Cl_2$ three times and the produce (110 mg) was obtained as an off white foam.

Preparation of Carboxyphenylethyl Cotinine Bromide (CPE Cotinine)

As shown in FIG. 1B, a solution of cotinine (95 mg) and bromoethyl benzoic acid (123.4 mg) in DMF (1 mL) was heated at 100° C. overnight. The solvent was removed and the residue was washed with $CH_2Cl_2$ three times to remove unreacted starting materials. The residue (154 mg) was used without further purification.

Preparation of Carboxycotinine Methyl Ester

To a suspension of carboxycotinine (344 mg) in 10 mL of MeOH was added 0.5 mL of concentrated $H_2SO_4$. The resulting solution was stirred overnight at room temperature. Solid $NaHCO_3$ was added to neutralize the solution and the solution was filtered. Methanol was removed. The residue was redissolved in $CH_2Cl_2$, washed with saturated $NaHCO_3$, dried over $Na_2SO_4$. Solvent was removed and the white powder (270 mg) was used without further purification.

Preparation of Hydroxymethyl Cotinine

To a solution of carboxycotinine methyl ester (270 mg) in methanol (10 mL) was added 400 mg $NaBH_4$ in portions. The suspension was stirred at room temperature for 4 hr. 1 mL of 20% HCl was added and was stirred for 15 min. The pH was adjusted to 10 with $NaHCO_3$ powder and NaOH solution. Methanol was removed and the aqueous was extracted five times with $CH_2Cl_2$. The organic layer was dried over $Na_2SO_4$ and the solvents was removed. The residue was purified by flash chromatography (10% MeOH in $CH_2Cl_2$) to give 188 mg product as an oil.

Preparation of Hydroxymethyl Cotinine Hemisussicinate (HCH)

As shown in FIG. 1C, to a solution of hydroxymethyl cotinine (33 mg) in 3 mL of benzene was added succinic anhydride (16 mg) and the solution was heated at 70° C. overnight. A white precipitate formed. Cooled to room temperature and decanted the benzene. The white powder was washed with ether a few times and the remaining white powder (43 mg) was used without further purification. TLC and NMR data confirmed the assigned structures. Purities of the cotinine derivatives are >90% by TLC.

Preparation of Cotinine Immunogens

Preparation of Carboxy-Cotinine-KLH Conjugate

A solution of carboxy-cotinine (22 mg), N-hydroxysuccinimide, NHS (11 mg) and N,N'-dicyclohexylcarbodiimide, DCC (22 mg) in dimethylformamide, DMF (1 ml) was stirred in room temperature for 1 hour. The mixture was then added to a solution of Keyhole Limpets Hemocyanin, KLH (20 mg) in 0.1 M Carbonate Buffer, pH9 and incubated for four hours, then dialyzed against four changes of PBS. Carboxy-Cotinine is depicted in FIG. 1D.

Preparation of Cotinine-Caproic-KLH Conjugate

A solution of cotinine-caproic acid, CCA (3 mg), NHS (6 mg) and DCC (12 mg) in DMF (0.6 ml) was stirred at room temperature for 1 hour. The mixture was then added to a solution of KLH (5 mg) in PBS (3 ml). The mixture was stirred for four hours at room temperature and then dialyzed against four changes of PBS.

Preparation of Carboxyphenylethlyl-Cotinine-KLH Conjugate

A solution of carboxyphenylethyl-cotinine, CPEC (2 mg), NHS (1.2 mg) and EDC (2.4 mg) in DMF (0.1 mg) was stirred at room temperature for 1.5 hour. The mixture was then added to a solution of KLH (10 mg) in 0.083M Phosphate Buffer in 0.9M NaCl, pH 7.2 (1 ml). After overnight incubation, the mixture was dialyzed against four changes of PBS.

Preparation of Hydroxymethyl-Cotinine-Hemisuccinate-KLH Conjugate

A solution of Hydroxymethyl-Cotinine-Hemisuccinate, HCH (3.2 mg), NHS (3.2 mg) and DCC (6 mg) in DMF (2.3 ml) was stirred at room temperature for 1 hour. The mixture was then added to a solution of KLH (10 mg) in 0.083 M Phosphate Buffer in 0.9M NaCl, pH 7.2 (1 ml). After overnight incubation, the mixture was dialyzed against four changes of PBS.

Immunization Protocol

Mice, Balb C or Swiss Webster, were injected first with cotinine derivative-KLH conjugate at 10 microgram per mouse with CFA. After three weeks the mice were boosted with 10 microgram of immunogen per animal with IFA. Two weeks after the first boost, the mice were bled and the antisera were tested in Elisa for Anti-cotinine antibody titer. Second and subsequent boosts, if used, were done at three week intervals with 10 microgram of immunogen per dose. Testing was done two weeks after each boost.

Four different immunization routes were used:
Route A: First injection and all three boosts were done with the same immunogen, Carboxy-cotinine-KLH.
Route B: First injection and next three boosts were done with the same immunogen, Cotinine-caprioc-KHL. The fourth boost was done with immunogen CPEC-KLH.
Route C: First injection was done with Carboxy-cotinine-KLH and first boost was done with HMCH-KLH.
Route D: First injection was done with HMCH-KLH and first boost was done with Carboxy-cotinine-KLH.

Immunization Route A

Figure 3:
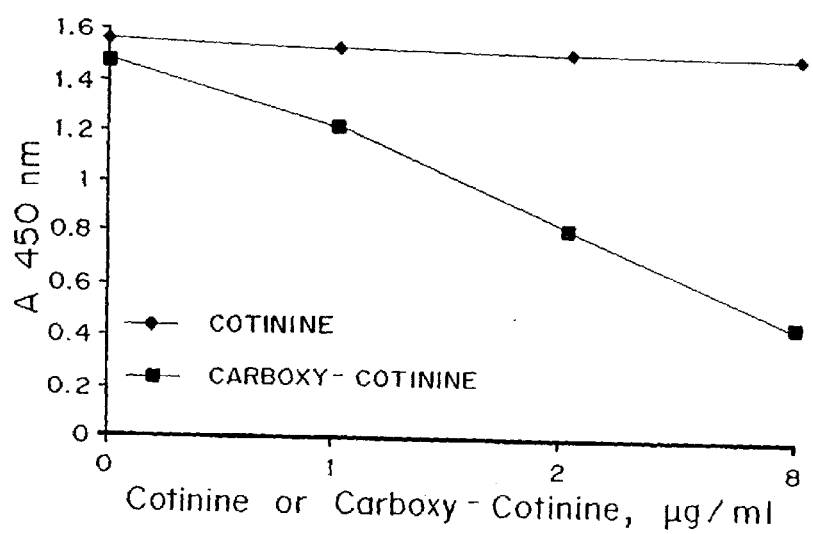
FIG. 3 is a graph of antibody binding to cotinine (diamonds) or carboxy-cotinine (squares) at concentrations of between 0 and 8 micrograms/ml.

Three Balb C mice were immunized. Antisera were tested for antibody titer in microtiter plate Elisa using carboxy-cotinine derivative conjugated to bovine gammaglobulin as a solid phase. The amount of antibody bound to the plate was detected by goat anti-mouse IgG antibody labeled with peroxidase. Peroxidase was assayed with TMB substrate. Results on antisera titration are presented in FIG. 2. Subsequent boosts did not improve titers. After three boosts, the mouse with the highest antibody titer was selected for fusion. Fusion yielded a cell line 6F4.3.1 which produced monoclonal antibody to cotinine immunogen. The results are shown in FIG. 3.

Monoclonal antibody obtained with immunization route where the first injection and all boosts were done with the same immunogen, Carboxy-Cotinine-KLH, showed no specificity to free cotinine. The interaction of the antibody with Carboxy-Continine may be due to specificity for the carbonyl linker.

Immunization Route B

Five Babl C and five Swiss Webster mice were immunized. After each boost the antisera were tested for antibody titers and for specificity to continue. Antisera tested on CCA-BSA plates showed increasing antibody titers that reached level of 1:400,000 after the third boost. Testing for specificity was done in Elisa by determination of antibody binding to plates in the presence of free cotinine or negative and positive smokers urines. In this assay the plates were coated with Carboxy-continine derivative-BGG conjugate. After the third boost with the same immunogen CCA-KLH, the antibody showed no specificity to cotinine but interaction with positive urine. After the fourth boost with CPEC-KLH testing showed a great improvement in specificity to cotinine and stronger interaction with positive urine. Results are presented in Table 1.

TABLE 1

Evaluation of mouse serum after a boost with changed immunogen.

| Sample | Serum at 1:100 dilution after Third Boost A 450 nm | % BO | Serum at 1:200 dilution after Fourth Boost A 450 nm | % BO |
|---|---|---|---|---|
| Negative Urine | 0.465 | 100 | 1.384 | 100 |
| Positive Urine | 0.296 | 64 | 0.703 | 51 |
| Continine, 1 µg/ml | 0.572 | 123 | 0.947 | 68 |

The fourth boost increased antibody titers and improved specificity to Cotinine.

Figure 4:
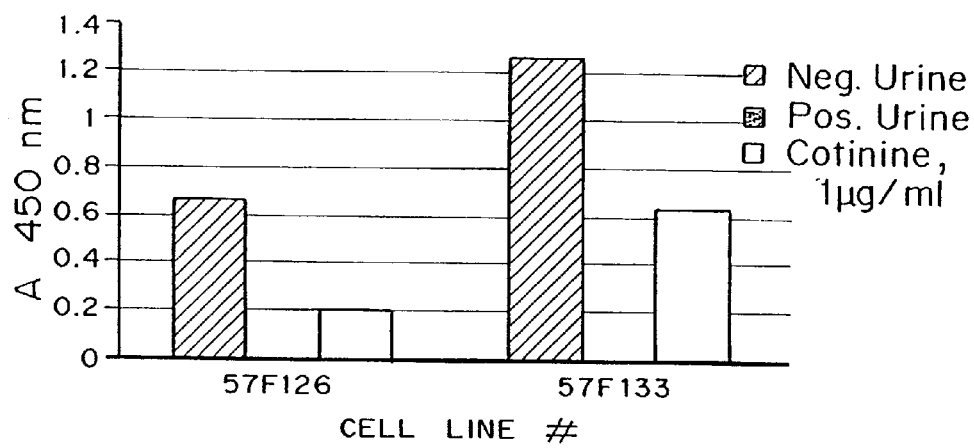
FIG. 4 is a graph of the interaction of two monoclonal antibodies, Mab 57F126 and 57F133 with cotinine (one microgram/ml, open squares) and urine samples (positive—containing cotinine, closed squares; negative—not containing cotinine, lines at baseline).

Two cells lines (57F126 and 57F133) producing monoclonal antibody were obtained in this study. The antibodies interacted strongly with smokers urines and showed also some reactivity with free cotinine as shown by FIG. 4.

Immunization Route C

Five Balb C mice were immunized in this study. After the first boost, the antisera were tested in Elisa on plates coated with Carboxy-cotinine-BGG conjugate. The antibody titers were very low, only 1:100. One mouse showed no response.

Immunization Route D

Figure 5:
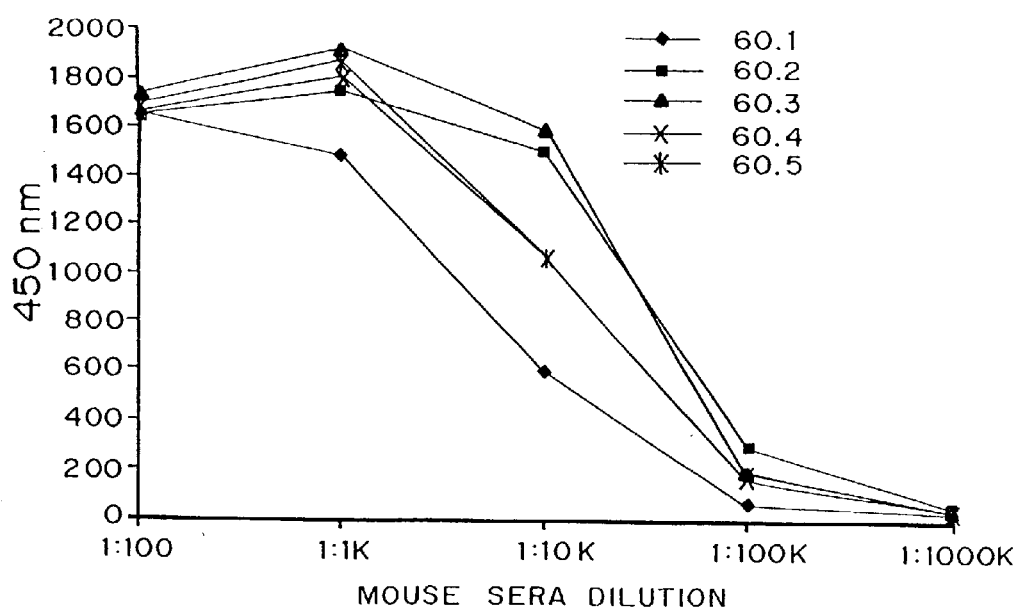
FIG. 5 is a graph of the antibody titer produced by immunization with a first immunogen followed by a boost with a second immunogen which differed from the first immunogen only by the structure of the linker. The first immunogen had hydroxymethyl heme succinate linking cotinine to keyhole limpet hemocyanine (KLH). The second immunogen included a carboxyl group linking continine to KLH. The first boost was three weeks following initial immunization. Ten micrograms/mouse was used for each immunization.

Five Babl C mice were immunized in this study. After the first boost, the antisera were tested in Elisa on plates coated with HMCH-BGG conjugate. The antibody titers were very high above between 1:100,000 and 1:100,000 (see FIG. 5).

Testing for specificity was done in Elisa by determination of inhibition if antibody binding to plates in the presence of free cotinine and negative and positive urine samples. In this assay plates were coated with CPEC-BGG conjugate. Antiserum from mouse # 60.2 had the best characteristics and was selected for fusion. The antiserum showed total inhibition of antibody binding to the plate by positive smokers urine and 90% inhibition by free cotinine (see Table 2).

TABLE 2

Testing of mouse serum in Elisa.

| Sample | Serum at 1:100 dilution after Third Boost | |
|---|---|---|
| | A 450 nm | % BO |
| Negative Urine | 0.349 | 100 |
| Positive Urine | 0 | 0 |
| Continine, 1 μg/ml | 0.033 | 9 |

Figure 6:
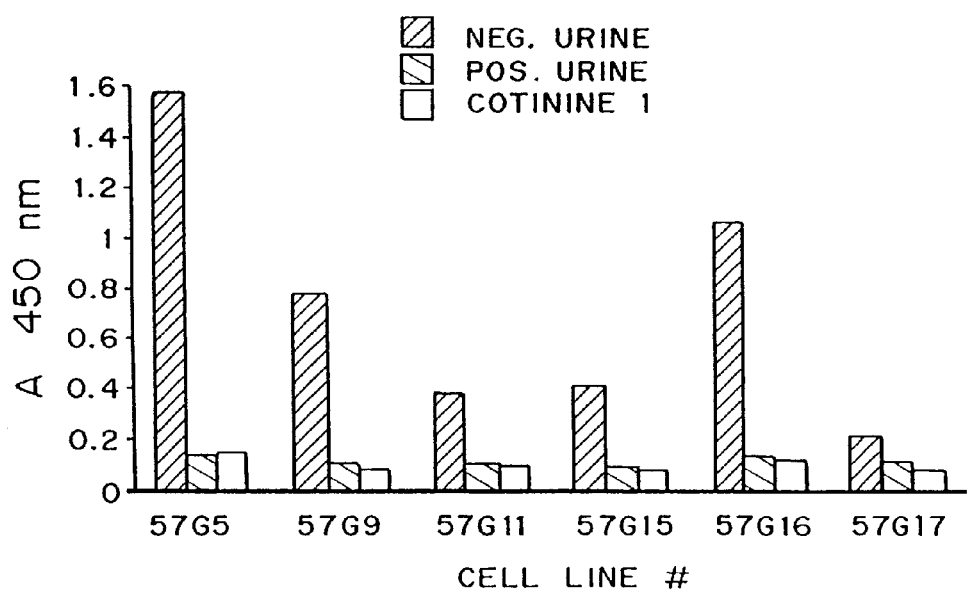
FIG. 6 is a graph of antibody binding of several monoclonal antibodies with cotinine (one microgram/ml, open squares) and urine samples (positive—containing cotinine, closed squares; negative—not containing cotinine, lines at baseline).
Figure 7A:
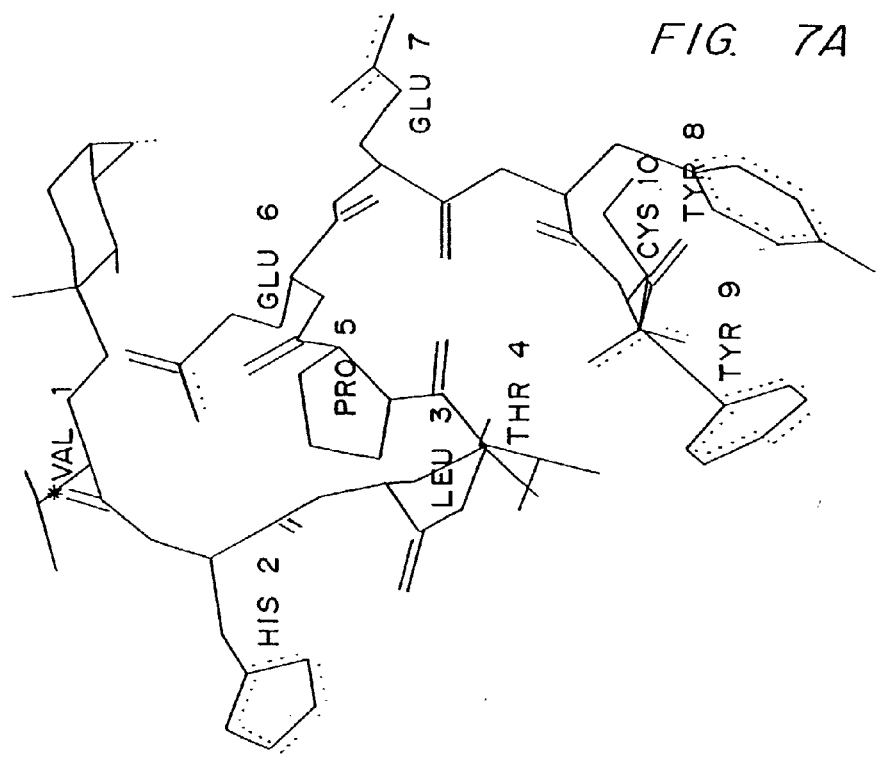
FIG. 7A is a Hyperchem model of the native sequence of the glycated Val-His-Leu-Thr-Pro-Glu-Glu-Tyr-Tyr-Cys (SEQ ID NO:5), the histidine residue is prominent.
Figure 7B:
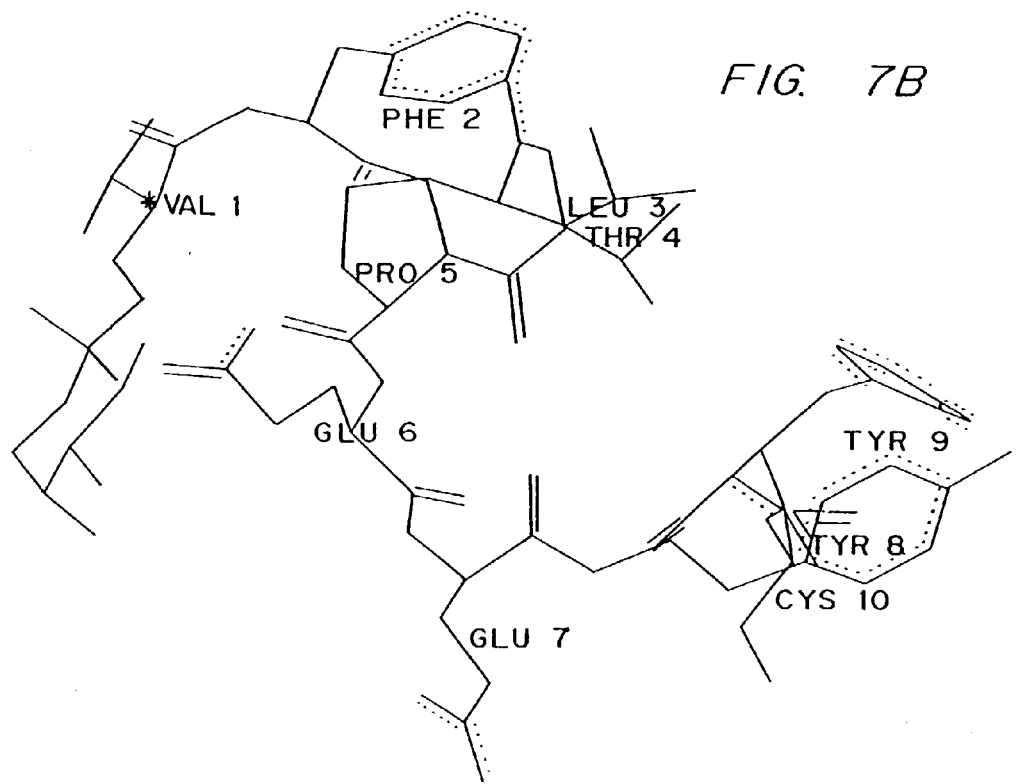
FIG. 7B is a Hyperchem model showing that when the histidine residue is replaced by phenylalanine, the residue is still prominent and not in the interior position one would imagine if the charge were neutralized by ionic interaction with an interior residue (SEQ ID NO:6).
Figure 8A:
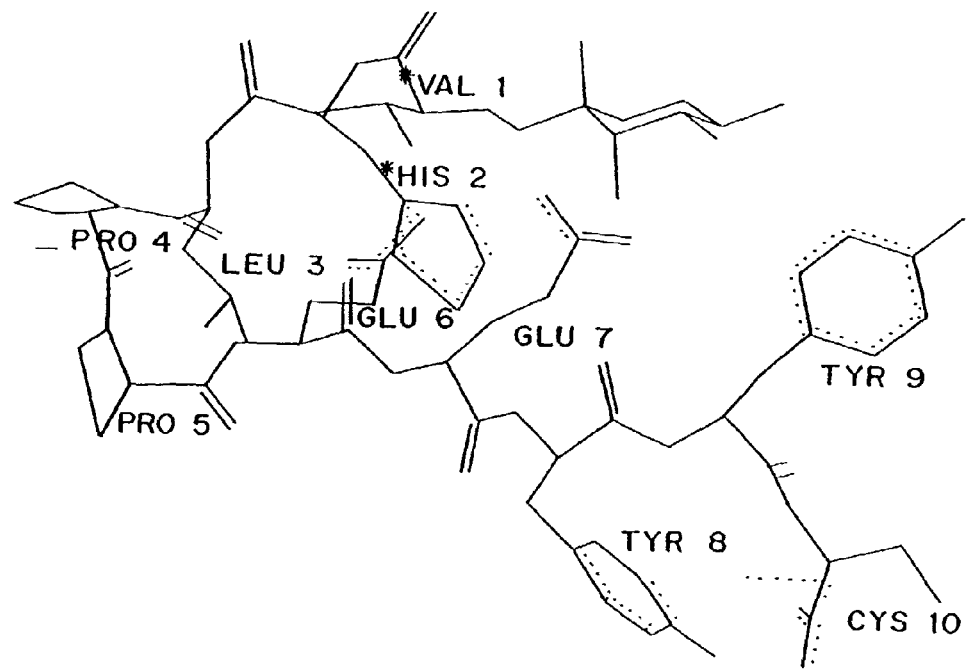
FIG. 8A is a Hyperchem model showing positioning the His imidazole ring in the interior of the folded peptide, by replacing the threonine at residue four with a proline to position the imidazole ring of histidine in an interior position while prominently displaying the glycated valine and backbone of histidine (SEQ ID NO:7).
Figure 8B:
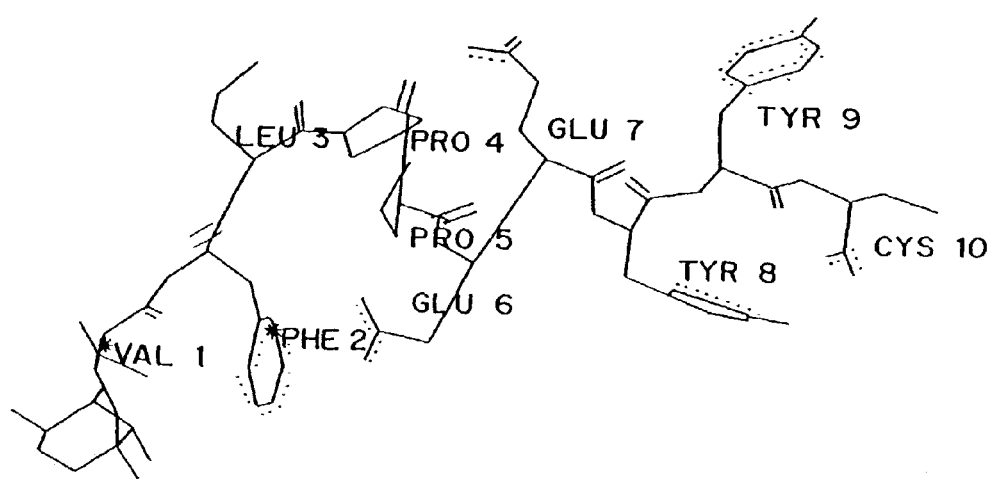
FIG. 8B is a Hyperchem model which, while not being a model of the 2-amino-3-furylpropionyl (Her) but utilizing phenylalanine as a Her mimic, indicating that one will achieve the proper orientation and steric conformation since the phenyalanine ring is bulkier than a furan ring and one would therefore expect that with the furan ring the ring would assume a more closed position similar to FIG. 8A.

Fusion yielded 17 cells which produced cotinine specific monoclonal antibody. Ascites were produced from the six best cells lines; 57G5, 57G9, 57G11, 57G15, 57G16 and 57G17. The results are shown in Table 3 and FIG. 6.

TABLE 3

Testing of hybridoma supernatants at 1:20 dilution in Elisa with free cotinine and urine samples.

| Sup# | Absorbance at 450 nm | | Cotinine (1 μg/ml) |
|---|---|---|---|
| | Neg. Urine | Post. Urine | |
| 57G5 | 1.578 | 0.145 | 0.151 |
| 57G9 | 0.775 | 0.11 | 0.079 |
| 57G11 | 0.379 | 0.101 | 0.093 |
| 57G15 | 0.405 | 0.09 | 0.073 |
| 57G16 | 1.054 | 0.128 | 0.108 |
| 57G17 | 0.205 | 0.1 | 0.072 |

EXAMPLE 2

Preparation of Hb A1C Immunogens and Immunization Protocols to Produce Highly Specific Antibodies It is difficult to get an antibody to distinguish between HbAo and HbA1c, as the difference is only one small sugar molecule. Sugars are poor immunogens and indeed the antibody methods on the market generally do not distinguish between a sugar and any other small change at the sugar site. General methods have therefore been developed to increase the immunogenicity of these glycoproteins and other poor immunogens, by altering the immunogenicity of the immunodominant epitope(s). The method utilizes an immunogen which is composed of a glycated peptide mimic of the glycated peptide sequence which is the target epitope, wherein the peptide mimic is constructed to conformationally mimic the conformation of the peptide in the native protein, the peptide mimic contains no charged groups or other immunodominant group, and the peptide mimic is connected to a spacer sequence equivalent to a peptide spacer of between one and thirty amino acids in length, which serves to position the peptide epitope in a conformation that approximates its conformation in the native protein. The peptide mimic and spacer can be linked to a carrier molecule. This method has been used to produce an antibody to the glycated protein HbA1c, wherein the peptide mimic includes a valine modified by addition of a glucose molecule, an analog of Histidine which does not bear a charge in the immunizing structure, allows orientation of the peptide so that the immune response can be directed to the side of the peptide chain oriented oppositely to the ring, and is of a size that the conformation of the peptide mimics the conformation of the peptide in the native molecule (2-amino-3-furylpropionyl), a leucine or an analog thereof which allows binding to an antibody preferentially recognizing Hb A1c such as 82D259, and a threonine or an analog thereof which allows binding to antibody number 82D259.

One of the problems with all the antisera based tests on the market is that they do not discriminate well between the various modifications that occur at the N terminal valine e.g. they do not discriminate well between an acetylated valine and one which is glycated. This is probably due to the fact that the antibody recognizes linear sequence and the amino acids are immunodominant to the sugar. The BM antibodies generated to a Hb $A_{1c}$ immunogen show high cross-reactivity with Hb $A_o$. Solid phase and solution phase binding studies were conducted to clarify how this antibody distinguished between the denatured and the native protein. In solid phase studies, the HbA1c protein was coated on a microtiter plate where the hydrophobic character of the plastic causes the denaturation of the protein, therefore exposing the linear peptide recognition domain. For solution phase studies, the protein was captured by an antibody on the plates during the assay, so that no denaturation occurred. In both cases, the antibody interacted with the anti Hb $A_{1c}$ antigen with no dramatic difference. There were two possibilities: 1. The purified Hb $A_{1c}$ was denatured during purification. 2. The antibody recognizes no difference between the denatured and native form of the protein 3. Exposure to the detergent used in lysing the red blood cells and during the Elisa essay was sufficient to denature the liquid phase HbA1c.

It was predicted that the HbA1c epitope was present on the surface of the native protein but that in the denatured state the epitope appeared quite different and contained an immunodominant moiety that was not present in the native conformation of HbA1c and HbAo. It was reasoned that as long as this immunodominant moiety was present the antibodies generated would not recognize a sugar and hence would be unable to distinguish between HbA0 and HbA1c in the native form.

A strategy was developed to create unique immunogens that result in a monoclonal that recognized native HbA1c. Since HbA1c is distinguishable from HbAo on a column it seems reasonable to assume that the epitope is accessible in the native molecule. Molecular models show the epitope on the surface and the BM antibody recognizes the epitope in at least nearly native format. It was reasoned that the conformation of the peptide was different in the native as opposed to the denatured peptide and that this might be result of the histidine: as a rule, charged groups are more immunogenic than non-charged groups.

An alternative explanation is that the Miles antibody recognizes the charged His side and this is the inside non-accessible face of the peptide in the native protein, whereas the BM antibody recognizes the outside or non charged side of the peptide. An immunogen was designed to recognize that one hypothesize to the configuration of the peptide in the native protein.

It was reasoned that it was needed to defocus the immune response from the linear peptide and the histidine and to focus the immune response on the fructose modification of the N terminal valine and the native conformation of the peptide. If the difference between the native Hb and denatured Hb molecule was the histidine charge, that charge could affect orientation (which was the result of histidine having a salt bridge type of interaction with an internal portion of the molecule) of the histidine. Thus it was reasoned that in the native form of Hb the conformation of the peptide was such that the imidazole ring oriented the histidine so that it was "tacked" by its charged ring nitrogen to the body of the protein. Thus the ring "faced the protein interior". To assure that this orientation and space filling conformation was achieved and that the charge did not become immunodominant an analog that had no charge was synthesized. Phenylalanine was also promising but was not used since an analog with the closest "space-filling" dimensions was need to get the highest specificity with a weak immunogen. It was reasoned that this non-charged peptide would interact with an antibody without the binding strength conferred by charge and thus one could improve immunogenicity by improving the "fit" or exactly mimicking the spatial relationships that would exist between the epitope and the binding site and thus it was aimed to provide an analog with the closest "space filling" dimensions reasoning that this would result in a conformation that was closest to that of the epitope on the surface of the molecule.

It was hypothesized that the Histidine residue might be immunodominant in the peptide immunogen sequence, but that in the native protein in the Histidine could be in a salt bond with another residue. Hence an antibody that depended on interaction of a negatively charged binding site residue with the positively charged His might not recognize native $HbA_{1c}$. This hypothesis was tested utilizing two peptides in competitive assays:

Val-His-Leu-Thr-Pro-Glu-Glu-Tyr-Tyr-Cys Termed (His) (SEQ ID NO:5) and Val-Phe-Leu-Thr-Pro-Glu-Glu-Tyr-Tyr-Cys Termed (Phe) (SEQ ID NO:6).

It was reasoned that Phe filled a similar space as His but had no charge and so could be used to monitor the dependence of antibody affinity on the presence of a charged His residue. In this experiment, $HbA_{1c}$, anti $HbA_{1c}$ BM and Miles antibodies, and the peptides were incubated in microtiter plate wells previously coated with rabbit anti-Human Hb. Both peptides are shown to equally inhibit the interaction of BM antibody with $HbA_{1c}$ as well as $HbA_o$. However, when the Miles antibody was tested, there was a big difference in inhibition of the interaction of Mab with $HbA_{1c}$, the His-peptide showed strong inhibition while the Phe-peptide did not interfere. The data suggests that His charge is integral to the Miles' antibody binding to $HbA_{1c}$, however, it is not important in BM antibody's interaction with $HbA_{1c}$. This suggests that the Miles antibody selectivity for the denatured form of $HbA_{1c}$ is actually a requirement for a charged accessible His and the BM antibody which binds equally well to both denatured and native $HbA_{1c}$ is not affected by the charge on His. This suggests that one should not use a peptide with a charged His residue. The molecular models discussed in detail below and shown in FIGS. 7A and 7B and 8A and 8B support these conclusions.

This immunogen is a peptide-protein conjugate containing the sequence Fructose Val H Y Y . . . —R. Where H is an uncharged analog of Histidine and Y is the native or other peptides providing up to 20 or more amino acids and R is a protein. In a preferred embodiment, H is a structural analog of His with imidazole ring substituted by a furan ring, 2-amino-3-furylpropionic acid, hereafter, "Her".

It has been shown that the peptide with H=Phe interacts with BM antibody similar to the peptide with His. The advantage of using Her in the immunogen is to eliminate the charge on the second residue, therefore focusing the immune recognition on fructose-Val-uncharged His Leu Thr while maintaining the size of the imidazole ring. It was believed that this approach had the potential to generate an antibody to recognize native $HbA_{1c}$.

It was hypothesized that the charge on the histidine in the linear peptide was the immunodominant epitope when one immunized with the linear peptide and that in the native molecule this charge could be neutralized by interaction with another amino acid. In this model the charge carrying nitrogen of the imidazole ring is oriented towards the interior of the molecule. Therefore a peptide with an analog of histidine with neutral charge (hereafter "Her") was synthesized. The peptide was modeled using a molecular modeling program to provide a peptide that oriented the charge carrying position towards the interior of the peptide.

The immunogen which was designed had the sequence:

```
Fructosyl-Val-2-amino-3-furanylpropionyl-Leu-Pro-Pro-Glu-Glu-Tyr-Tyr-Cys (SEQ ID NO:4)
          1          2                     3   4   4   5   6   6   7   8
``` which can form part of a longer immunogen having the following formula:

Fructose-Val-Her-3-4-5-6 . . . -X-R, where residue 1 is a valine (or analog thereof) modified by addition of a glucose molecule;

where residue two is an analog of Histidine that does not bear a charge in the immunizing structure;

where residues three to twenty allow the orientation of the peptide so that the immune response can be directed to the side of the peptide chain oriented oppositely to the ring; and where residue two is of a size and charge that the conformation of the peptide mimics the conformation of the peptide in the native molecule;

where residue three is leu or an analog thereof which allows binding to antibody number 82D259;

where X is a linker and where preferably different linkers or linker method are used at each immunization or where Y is varied between each immunization; and where R is a carrier that allows a vigorous immune response.

This immunogen was used to prime to the peptide and the animal subsequently boosted with immunogens where linkages are different.

Molecular Modeling.

Molecular modeling of the peptide was accomplished using the program, Hyperchem (Hypercube, Inc. Waterloo, Ontario, Canada). As can be seen in FIG. 7A, in the native sequence of the glycated Val-His-Leu-Thr-Pro-Glu-Glu (SEQ ID NO:5), the Histidine residue is prominent. When Histidine is replaced by Phenylalanine, FIG. 7B the residue is still prominent and not in the interior position one would imagine if the charge were neutralized by ionic interaction with an interior residue. The threonine at residue four was replaced with a proline to position the His imidazole ring to the interior of the folded peptide. FIG. 8A shows that this placed the imidazole ring of histidine in an interior position while prominently displaying the glycated valine and backbone of histidine. One could not model with 2-amino-3-furylpropionic acid (Her) but utilizing phenylalanine as a Her mimic, FIG. 8B the model indicated that one would achieve the proper orientation and steric conformation (the phenyalanine ring is bulkier than a furan ring and so one would expect that with the furan ring the ring would assume a more interior position. Accordingly for an immunogen we utilized the sequence Fructosyl-Val-2-amino-3-fur-anylpropionyl-Leu-Pro-Pro-Glu-Glu-Tyr-Tyr-Cys (SEQ ID NO:4).

It was maintained that Her, whether 2-amino-3-furanylpropionic acid or phenylalanine or some other analog of these, is not an obvious analog of Histidine in this peptide. 2-amino-3furanylpropionic acid is not a naturally occurring amino acid and is not commercially available. Her's substitution in the peptide abolished binding with the Miles antibody. Her serves a different function than an analog. An analog is by definition something that is similar in function but not in origin and structure in immunochemistry it refers to an equivalent immunologic substitute. The purpose of Her is to abolish the immunodominance and charge of histidine so it does not serve this purpose.

The first immunization effort with the Her Peptide immunogen generated only a modest number of viable reactive wells for each fusion and out of 10 animals and fusions only one clone (clone 87) was obtained that met the desired specifications. This clone was not stable. The immunogenicity (titers) of this immunogen was relatively low and the desired antibody clones generated by this immunogen were a small percentage of the total antibody response. Thus, while this strategy might eventually generate an antibody it was looking for a needle in a haystack. To increase the chance of success a strategy was developed that increases the immunogenicity of weak immunogens. This change in immunizing strategy is thus designed to increase the size of the "haystack" and assumes that the number of "needles" remains at a fixed percentage of the "hay". With this strategy one was able to increase the number of reactive clones from one fusion to six hundred and to select six clones with potential to have high titer, high specificity and desired reactivity.

One reason that this strategy may have so successfully assisted in the generation of antibodies to HbA1c is that the weaker the immunogen, the more important it is that the immune response of the animal is directed away from the linker. Since the conformation of the peptide is dependent on the linker and the protein linkage, another function served by changing the portion of the peptide that serves to link the peptide to the carrier protein is that changing linkers avoids boosting to a linker induced epitope conformation.

The strategy utilized to overcome the weak immunogenicity of glycated residue peptide has been described in U.S. Ser. No. 60/059,377 Entitled "Method to Improve Immunogenicity of Antigens and Antibody Responses". This strategy is hereafter referred to as "focused immunization". In immunizing with poor immunogens the predominant immunological response may be to the linker or to other non-relevant portions of the peptide immunogen and that one could change the focus by changing the linker (but not the carrier protein) with each immunization. The linker specific response and/or the response to a linker induced epitope conformation is reduced and focused the secondary response on the desired epitope.

It was not until one immunized utilizing the Focused Immunization protocol that one obtained sufficient clones (about 600 reactive clones from fusion number 82D) to allow isolation of a monoclonal 82D259 with the desired characteristics, i.e., an antibody with increased specificity; an antibody which eliminates the need for pretreatment and which can be used in a variety of formats for clinical and home testing; and an antibody that can be produced economically.

Preparation of Immunogens

Furylacrylic acid, (S)-4-phenylmethyl-2-oxazolidone, pivaloyl chloride, FMOC-C1, 2% Pd-SrCO$_3$, Raney-Nickel, n-BuLi, KHMDS, triethyl amine, 30% H$_2$O$_2$, NaOH, HCl, Na$_2$SO$_4$, THF, NaHCO$_3$, acetic acid, Na$_2$SO$_3$, trifluroacetic acid, citric acid, and pyridine were purchased from Aldrich. Glucose and beta-mercaptoethanol were purchased from Sigma. KLH-maleimide was purchased from Pierce. Ethanol, CH$_2$Cl$_2$, ethylacetate, diethyl ether, methanol, and petroleum ether were purchased from VWR Scientific. Trisyl azide was prepared as in the literature (Harmon, R. E.; Wellman, G.; Gupta, S. K. *J Org. Chem.* 1973, 38, 11-16.) The peptide was synthesized by AnaSpec, Inc., 2020 Lundy Avenue, San Jose, Calif. 95131.

Preparation of 3-furylpropionic Acid

Furylacrylic acid (1 g) was dissolved in 15% NaOH (100 mL, small amount of ethanol was added to facilitate it dissolve). Hydrogenation was then carried out with catalytic amount of 2% Pd—SrCO$_3$ for two days. The mixture was filtered, acidified with 6 N HCl, extracted with CH$_2$Cl$_2$, dried over Na$_2$SO$_4$, and the solvent was removed. The residue was recrystalized from petroleum ether at −20 C as a white powder.

Preparation of (S)-3-(1'-Oxo-3-furylpropyl)-4-phenylmethyl-2-oxazolidinone

To a solution of 3-furylpropionic acid (163 mg) in THF (4 mL) cooled to −78 C was added triethyl amine (0.21 mL) and pivaloyl chloride (0.16 mL). The mixture was allowed to warmed to 0 C after 15 min. And was stirred at 0 C for 45 min, then the mixture was cooled back to 78 C.

To a solution of (S)-4-phenylmethyl-2-oxazolidone (248 mg) in 10 mL THF, cooled to −78 C, was added to 0.87 mL n-BuLi (1.6 M in hexane). The resulting solution was added to the above mixture and was stirred for 10 min. at −78 C. The mixture was then allowed to warm to 0 C. and was stirred for 2 hr. The mixture was quenched with saturated NaHCO$_3$ and diluted with diethyl ether. The aqueous layer was extracted with diethyl ether and the combined organic layer was washed with brine, dried over Na$_2$SO$_4$, and concentrated in vacuum. The residue was purified by flash chromatography (1:1 diethyl ether and petroleum ether).

Preparation of [S-(R*, R*)]-3-(2'-azido-1'-oxo-3-furyl-propyl)-4 phenylmethyl-2-oxazolidinone To a solution of (S)-3-(1'-oxo-3-furylpropyl)-4-phenylmethyl-2-oxazolidinone (5.7 g) in 100 mL THF cooled to −78 C was added to 40 mL of KHMDS (0.5 M in toluene) solution dropwise. The mixture was stirred at −78 C for 20 min. A cold solution of trisyl azide (7.4 g) in 40 mL THF was added to the reaction mixture and was stirred at −78 for 15 min. The reaction mixture was then quenched with 3.2 mL acetic acid and was allowed to warm up to room temperature. After stirring for 2 hr., the reaction mixture was diluted with diethyl ether, washed with saturated NaHCO$_3$, brine, dried over Na$_2$SO$_4$, and concentrated in vacuum. The residue was purified by flash chromatography (1:1 diethyl ether and petroleum ether) to give the product as an oil.

Preparation of (S)-2-azido-3-furylpropionic Acid

To a solution of [S-(R*, R*)]-3-(2'-azido-1'-oxo-3-furyl-propyl)-4-phenylmethyl-2-oxazolidinone (4.6 g) in 150 mL THF and 20 mL H$_2$O was added 5.5 mL of 30% H$_2$O$_2$ at 0 C and the mixture was stirred for 2 hr. at 0 C. Na$_2$SO$_3$ (7.6 g) was added and then the mixture was stirred for another 10 min. THF was removed, diluted with $H_2O$, extracted with $CH_2Cl_2$, acidified with citric acid to pH3, extracted again with ethylacetate, washed with brine, dried over $Na_2SO_4$, and concentrated in vacuum. The residue was purified by flash chromatography (1% acetic acid in ethylacetate) to give the product as an oil.

Preparation of (S)-2-amino-3-furylpropionic Acid trifluroacetic Acid Salt

To a solution of (S)-2-amino-3-furylpropionic acid (1.4 g) in 200 mL ethanol was added Raney Nickel (0.5 g, washed with H2O twice and ethanol twice). The mixture was hydrogenated overnight. Ethanol was removed and the residue was dissolved in H2O with a small amount of trifluroacetic acid. The solution was extracted with ethylacetate, the water was removed, the product was azeotrophed with toluene, and the residue was dried under vacuum. The product was dissolved in methanol and was titrated with Et2O to give a white powder.

Preparation of N-FMOC-(S)-2-amino-3-furylpropionic Acid (S)-2-amino-3-furylpropionic acid trifluroacetic acid salt (0.47 g) was dissolved in 30 mL of 10% Na2CO3 and 5 mL of dioxane and was cooled to 0 C. A solution of FMOC-Cl (0.53 g) in 10 mL was added dropwise. The mixture was then stirred for 15 min. at 0 C. and 2 hr at room temperature. The mixture was diluted with H2O, extracted with diethyl ether, and acidified with citric acid. The mixture was filtered and washed with H2O until neutral. The solid was then dissolved in ethylacetate, dried over Na2SO4, concentrated in vacuo to give the product as a white foam.

Preparation of Val-Her-Leu-Pro-Pro-Glu-Glu-Tyr-Tyr-Cys (SEQ ID NO:4)

The synthesis of this peptide was completed by Ana Spec, Inc. using peptide synthesizer.

Preparation of Glycated Val-Her-Leu-Pro-Pro-Glu-Glu-Tyr-Tyr-Cys (SEQ ID NO:4)

Peptide Val-Her-Leu-Pro-Pro-Glu-Glu-Tyr-Tyr-Cys (SEQ ID NO:4) (20 mg) and glucose (86 mg) was azeotrophed with pyridine twice. The residue was then dissolved in pyridine (2 mL) and the mixture was stirred at dark for 4 days. Pyridine was then removed.

Preparation of Glycated-Val-Her-Leu-Pro-Pro-Glu-Glu-Tyr-Tyr-Cys (SEQ ID NO:4) and KLH Conjugates Conjugate 1: 2.5 mg of glycated-peptide in 1 mL of phosphate buffer (75 mM phosphate, 0.9 M NaCl, pH 7.2) was mixed with 5 mg KLH-maleimide in 0.5 mL $H_2O$. The mixture was stirred at room temperature for 2 hr. To this was then added 1 µL of beta-mercaptoethanol (14.3 M) and was stirred for another 2 hr. The mixture was dialyzed against 4 changes of phosphate buffer (83 mM phosphate, 0.9 M NaCl, pH 7.2).

Conjugate 2: 4 mg of glycated-peptide in 1 mL of $H_2O$ was mixed with 4 mg of KLH in 0.4 mL $H_2O$. To above mixture, 30 mg of EDC was added and mixture was incubated 4 hr at room temperature with pH kept at 5.5-6.0. The mixture was dialyzed against 4 changes of PBS.

Immunization of Animals and Screening for Specific Antibody Immunization Protocol Mice, Swiss Webster, were injected first with Glycated-Val-Her-Leu-Pro-Pro-Glu-Glu-Tyr-Tyr-Cys-KLH (SEQ ID NO:4) (conjugate #1) at 10 microgram per mouse with CFA. After three weeks, mice were boosted with conjugate #2 at 10 microgram per animal with IFA. Two weeks after first boost mice were bled and antisera were tested in Elisa for antibody titer. Second and third boost were done in three weeks intervals with conjugate #1 at 10 microgram of immunogen per dose. Testing was done two weeks after each boost.

Testing of Mice Bleeds

Mice sera at different dilutions were incubated with microtiter plates coated with solid phase antigen which was an equal mixture of Glycated-Val-Her-Leu-Pro-Pro-Glu-Glu-Tyr-Tyr-Cys (SEQ ID NO:4) and Glycated-Val-Phe-Leu-Pro-Pro-Glu-Glu-Tyr-Tyr-Cys (SEQ ID NO:8) conjugated to maleimide activated rabbit gamma globulin. Antibody titers after first boost were in the range of 1:10,000 to 1:100,000 and after second boost were in the range of 1:100,000 to 1,000,000. Mouse #3.4 showed titer 1:1,000,000 and was used for fusion after third boost.

Figure 9:
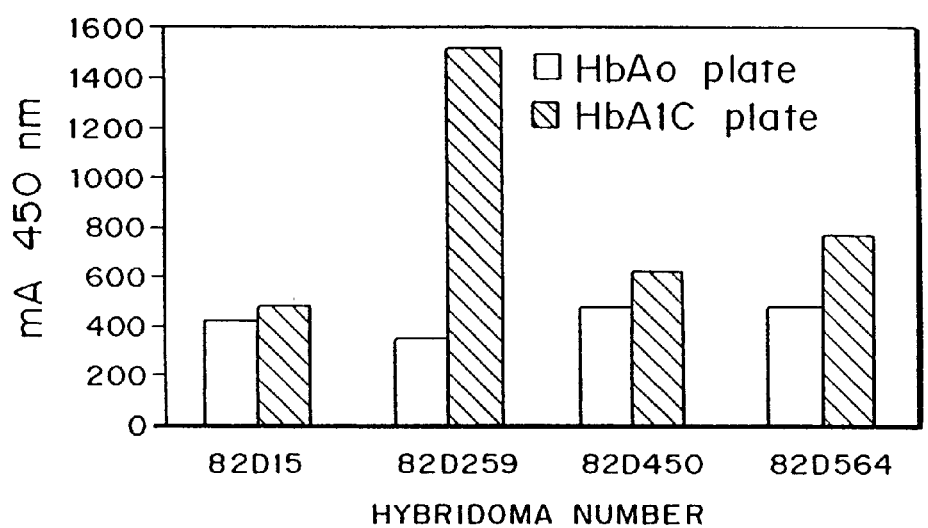
FIG. 9 is a graph showing screening of hybridomas from fusion 82D for clones reactive with HbA1c (but only minimally reactive with HbAo) in an Elisa System. Plates were coated with purified HbA1c or HbAo. A 2.5 fold dilution of fusion supernatant was incubated for 1 hour followed by wash and 1 hour incubation with Peroxidase labeled anti-mouse. High absorbance value correlates with high recognition of the plate coating material.

The fusion yielded hybridomas that bound both Hb Ao and Hb A1c, as shown by FIG. 9. Hybridoma 82D259 distinguished between HbAo and HbA1c best.

We claim:

1. A method for producing an antibody to the glycated protein HbA1c, comprising immunizing an animal with a conjugate comprising a hapten conjugated to a carrier, the conjugate hapten comprising a glycated peptide mimic of the glycated peptide sequence which is the target epitope, wherein the peptide mimic comprises amino acid residues sequentially numbered beginning with one, where residue one is a valine modified by addition of a glucose molecule, where residue two is an analog of Histidine which does not bear a charge in the immunizing structure, and allows orientation of the peptide so that the immune response can be directed to the side of the peptide chain oriented oppositely to the ring, and is of a size that the conformation of the peptide mimics the conformation of the peptide in the native molecule, where residue three is leucine or an analog thereof which allows binding to an antibody preferentially recognizing Hb A1c, and where residue four is threonine or an analog thereof which allows binding to antibody preferentially recognizing Hb A1c, wherein the peptide mimic is constructed to conformationally mimic the conformation of the peptide in the native protein, and wherein the peptide mimic contains no charged groups or other immunodominant group.

2. The method of claim 1 wherein the peptide mimic further comprises a peptide spacer of between one and thirty amino acids in length, which serves to position the peptide epitope in a conformation that approximates its conformation in the native protein.

3. The method of claim 2 wherein the peptide mimic is linked to a carrier protein selected from the group consisting of polylysine, keyhole limpet hemocyanine, and albumin.

4. The method of claim 1 wherein the Histidine analog is 2-amino-3-furylpropionyl.

* * * * *